(12) United States Patent
Salazar et al.

(10) Patent No.: US 6,451,023 B1
(45) Date of Patent: Sep. 17, 2002

(54) GUIDE BUSHING FOR CORING REAMER, STORAGE PACKAGE FOR REAMER ASSEMBLY, AND METHOD OF USE

(75) Inventors: Bartolome J. Salazar, Alpharetta, GA (US); Andrea Brasfield, St. Petersburg, FL (US); Mark A. Bellafiore, Clearwater, FL (US)

(73) Assignee: Linvatec Corporation, Largo, FL (US)

( * ) Notice: Subject to any disclaimer, the term of this patent is extended or adjusted under 35 U.S.C. 154(b) by 0 days.

(21) Appl. No.: 09/769,666

(22) Filed: Jan. 25, 2001

(51) Int. Cl.[7] .................................................. A61F 5/00
(52) U.S. Cl. ............................. 606/86; 606/79; 606/80
(58) Field of Search ........................... 606/83, 84, 80, 606/85, 79, 86, 87, 88, 96, 104

(56) References Cited

U.S. PATENT DOCUMENTS

| | | | |
|---|---|---|---|
| 4,621,961 A | * | 11/1986 | Gulistan |
| 4,690,418 A | * | 9/1987 | Smith |
| 4,696,308 A | * | 9/1987 | Meller et al. |
| 4,977,848 A | * | 12/1990 | Currey |
| 5,197,967 A | | 3/1993 | Wilson |
| 5,423,823 A | * | 6/1995 | Schmieding |
| 5,632,747 A | * | 5/1997 | Scarborough et al. |
| 5,928,238 A | * | 7/1999 | Scarborough et al. |
| 6,013,083 A | * | 1/2000 | Bennett |

* cited by examiner

Primary Examiner—Pedro Philogene
(74) Attorney, Agent, or Firm—Larson & Larson, PA; James E. Larson (57) ABSTRACT

A guide bushing for a coring reamer having a tapered member with its largest diameter at its first end so that the guide bushing frictionally engages an internal surface of the reamer with a line contact. The guide bushing has a passage sized to slidably receive a guide pin. In use, the bushing advances in the proximal direction within the coring reamer along a guide pin while the excavated bone enters the passageway through the reamer. A storage package specifically designed for the reamer assembly is employed to remove the excavated bone from within the reamer. The package has a closed distal end and an open proximal end closeable with a cap. With the coring reamer received in cantilevered fashion through a central opening of the cap of the tube, and with an adapter that couples the coring reamer to a handpiece installed, a wrench is placed over the adapter and turned while the user grips peripheral surfaces of the cap to prevent rotation of the coring reamer. A plunger is inserted through the opening through the coring reamer from the proximal end and is pushed through the reamer until the bone core and bushing fall out of the distal end of the coring reamer.

13 Claims, 9 Drawing Sheets

GUIDE BUSHING FOR CORING REAMER, STORAGE PACKAGE FOR REAMER ASSEMBLY, AND METHOD OF USE

BACKGROUND OF THE INVENTION

The present invention relates to a coring reamer. More particularly, it refers to an improved guide bushing for a coring reamer, a storage package for a coring reamer assembly, and a method of using the coring reamer.

In the prior art, it is well known to use a coring reamer to cut a cylindrical bone tunnel at a surgical site. The reamer is coupled to a handpiece that rotates the reamer to facilitate cutting a bone tunnel. For this purpose, the reamer has a cylindrical distal end with sharp teeth formed thereon.

It is also well known to guide such a reamer by employing a guide pin separately and previously driven into or through the bone at the surgical site. As the reamer cuts the bone tunnel, the reamer slides over the guide pin to guide its motion. While the prior art contemplates an interface between the guide pin and the reamer, one aspect of the present invention proposes an improvement thereover.

In U.S. Pat. No. 5,423,823 to Schmieding, the guide pin has an enlarged collar that guides the reamer over its peripheral edges. This collar is fixedly mounted on the guide pin or integrally formed therewith and facilitates removing the core from the coring reamer. A prior U.S. Pat. No. 4,696,308 to Meller et al. shows a guide pin with a cylindrical bushing having a cylindrical exterior and a passage therethrough allowing it to be freely slidably mounted over a guide pin. U.S. Pat. No. 5,197,967 to Wilson teaches a trephine instrument including a reamer with a blind passageway therethrough in which is freely slidably mounted a piston having enlarged distal and proximal flanges with the piston being spring biased into the distal direction. The piston is not easily removable from the trephine and the instrument is so designed that any bone core formed by the trephine can be removed by leaving the core attached at one end and pulling the instrument away so the core can be broken off at its distal end. None of this prior art has the advantages of the subject invention.

Applicants are aware of no known prior art relating to handling a reamed bone core other than simply pushing/pulling it out of a reamer onto a surface. Also applicants are not aware of any prior related to packaging suitable for storing coring reamers and usable thereafter to facilitate removal of a bone core from the reamer.

SUMMARY OF THE INVENTION

The present invention relates to an improved guide bushing for a coring reamer, a storage package for the reamer assembly, and a method of using the coring reamer. The present invention includes the following interrelated objects, aspects and features:

(1) In a first aspect, the present invention contemplates employing a coring reamer having a cylindrical passageway extending completely therethrough. The coring reamer has a proximal coupling enabling it to be coupled to an adapter which is coupled to a handpiece such as a drill or other instrument designed to impart rotary motion to the reamer. The distal end of the reamer includes a set of teeth surrounding the opening extending therethrough.

(2) The present invention further contemplates a guide bushing consisting of a tapered member having its largest diameter at its proximal end with respect to the reamer and wherein the guide bushing engages an internal cylindrical surface of the reamer with a line contact at its distal end. The guide bushing has a passage extending therethrough sized to slidably receive a guide pin. In a preferred embodiment, the guide bushing is pre-assembled with the coring reamer.

(3) Prior to the reamer being employed, a guide pin is driven into a bone at the surgical site. The reamer/bushing assembly is slid over the guide pin into contact with the bone. Alternatively, if the bushing and reamer are not pre-assembled, the bushing is slid over the guide pin into contact with the bone and the reamer is advanced over the guide pin until the bushing has entered the distal end of the passageway through the reamer.

(4) The handpiece is activated, causing the reamer to rotate, and the surgeon applies a forward pushing force in the distal direction, thereby causing the reamer to excavate a tunnel in the bone. As this excavation takes place, the bushing advances proximally within the reamer while the excavated bone enters the passageway through the reamer with the bone material engaging the distal surface of the bushing throughout the procedure.

(5) Once the tunnel has been formed through the bone, the guide pin, with the reamer attached and with the excavated bone material within the reamer, is removed from the surgical site. A storage package specifically designed for the storing and shipping of the reamer/bushing assembly and, in the preferred embodiment, attaching it to a handpiece is employed to remove the excavated bone core from within the reamer.

(6) The package includes a transparent tube having a closed distal end and an open proximal end, with the open proximal end being closable with a special cap having a central opening therethrough sized to receive, in coupling relation, the proximal coupling of the coring reamer. The proximal coupling of the coring reamer has a polygonal or other non-circular surface at one portion thereof that mimics a corresponding polygonal or other non-circular surface within the opening formed within the cap. The cap has an enlarged periphery allowing it to be gripped by the fingers of the surgeon or other person.

(7) After the tunnel has been formed, the coring reamer is placed through the cap of the tube, with the adapter that coupled the coring reamer to the handpiece installed on the reamer and extending outside the package tube. A wrench is placed over the adapter and is turned while the user grips the peripheral surfaces of the cap to prevent rotation of the coring reamer, thereby allowing the adapter to be removed from the coring reamer. Thereafter, a plunger is inserted through the opening through the coring reamer from the proximal end thereof and is pushed therethrough until the bone core and bushing fall out of the distal end of the coring reamer and into the tube. Thereafter, the bone core may be removed and the coring reamer, bushing, tube and cap disposed of properly. It should be noted that the storage package can be used to initially couple the coring reamer/bushing assembly to the coupling adapter for assembly on to the handpiece.

As such, it is a first object of the present invention to provide an improved guide bushing for a coring reamer, a storage package for the reamer assembly, and method of using these elements in performing surgery.

It is a further object of the present invention to provide such a device in which the guide bushing engages an inner cylindrical passageway through the coring reamer with a line contact to reduce frictional interaction therebetween.

It is a further object of the present invention to provide such a device wherein the guide bushing includes an internal passageway sized to slidably mount the guide bushing over a guide pin.

It is a still further object of the present invention to provide such a device wherein a package is provided to ship the reamer and bushing assembly to the user. Such package also is used to facilitate removal of a bone core therefrom after the reamer assembly has been used.

It is a still further object of the present invention to provide such a device wherein the package includes a cap having an enlarged periphery allowing the cap to be non-rotatably gripped by a surgeon to allow attachment and removal of a proximal adapter from the reamer.

It is a still further object of the present invention to provide such a device including a plunger sized and configured to slide though the opening through the reamer to allow removal of a bone core and the guide bushing after the reamer has been used.

These and other objects, aspects and features of the present invention will be better understood from the following detailed description of the preferred embodiments when read in conjunction with the appended drawing figures.

SPECIFIC DESCRIPTION OF THE PREFERRED EMBODIMENTS

With reference, first, to FIGS. 1–6, a coring reamer is generally designated by the reference numeral 10 and is seen to include an elongated cylindrical tube 11 having an open distal end 13 surrounded by peripheral teeth 15. A cylindrical passageway 17 (FIG. 7) extends completely through the reamer 10.

With further reference to FIGS. 1–6, the reamer 10 includes a proximal end 19 consisting of a coupling 21 designed to couple the reamer 10 to an adapter 23 (FIG. 11) designed to couple the reamer 10 to a handpiece (not shown) adapted to rotate the reamer 10 in a manner well known to those skilled in the art. The proximal coupling 21 includes a distal portion 25 having a hexagonal periphery and a proximal portion 27 having a cylindrical periphery. The interface between the adapter 23 and the proximal coupling 21 consists of a threaded interconnection (not shown).

Figures 1, 2:
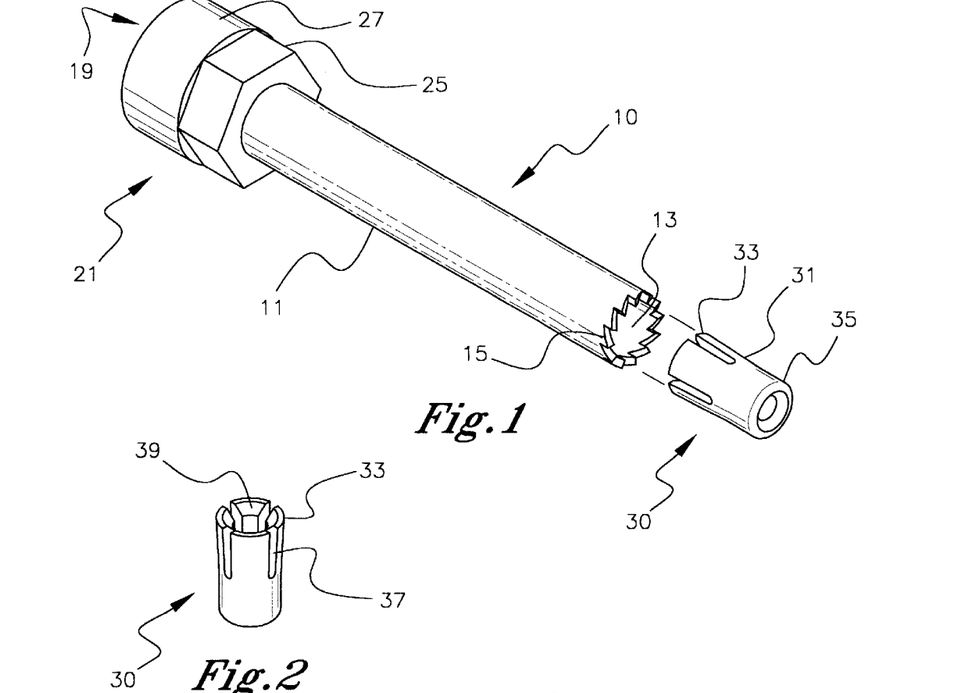
FIG. 1 shows an exploded perspective view of a coring reamer and a flared bushing in accordance with the teachings of the present invention.
FIG. 2 shows a side perspective view of the bushing.
Figure 3:
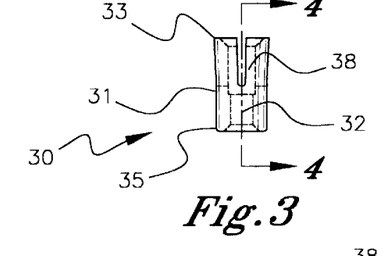
FIG. 3 shows a side plan view of the bushing.
Figure 4:
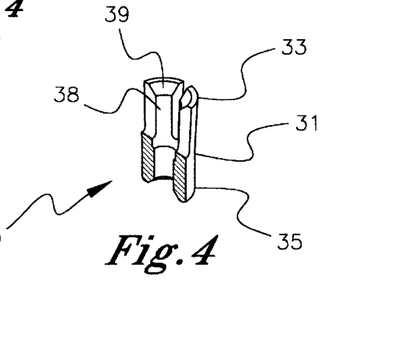
FIG. 4 shows a side cross-sectional view of the bushing.

With particular reference to FIGS. 1–4, a flared bushing is generally designated by the reference numeral 30 and is seen to include an outer wall 31 that is tapered from its widest dimension 33 (see FIG. 4) at the proximal end thereof to its narrowest dimension 35 (see FIG. 4) at its distal end. Dimension 35 is approximately equal to the cross-section of the passageway 17 to act as a centering device. With reference to FIG. 2, a plurality of slots 37 are provided extending distally from the proximal end 33 and a conical surface 39 defines the most proximal portion of a passage 38 extending centrally through the bushing 30. The conical surface 39 is a "lead-in" which facilitates alignment of plunger 80 with bushing 30 as will be understood below with reference to FIG. 13. The diameter of the outer wall 31 at the proximal end 33 of the bushing 30 is sized to facilitate slidable receipt of the bushing 30 within the passageway 17 through the reamer 10 in such a manner that the end 33 of the bushing 30 frictionally engages the passageway 17 of the reamer 10 with a line contact. When the longitudinal axis 32 (FIG. 3) of the bushing 30 is aligned with the longitudinal axis of the reamer 10, only the end 33 of the bushing 30 engages the inner walls of the passageway 17 of the reamer 10.

Figure 6:
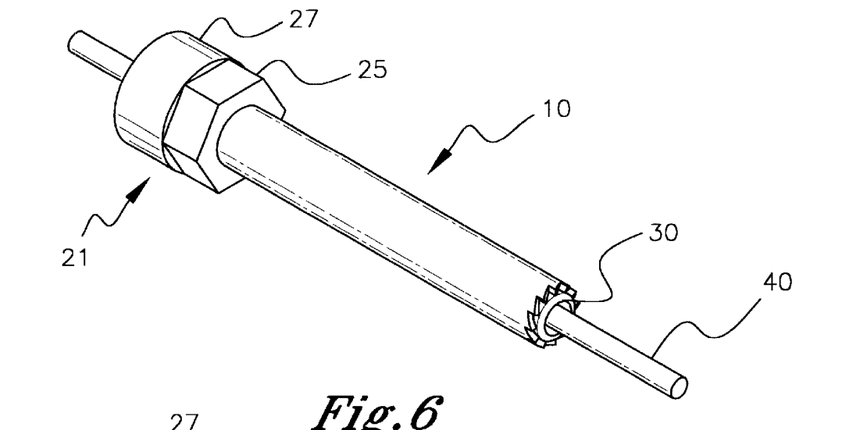
FIG. 6 shows a view similar to that of FIG. 5 but showing the coring reamer extended over a guide pin.
Figure 7:
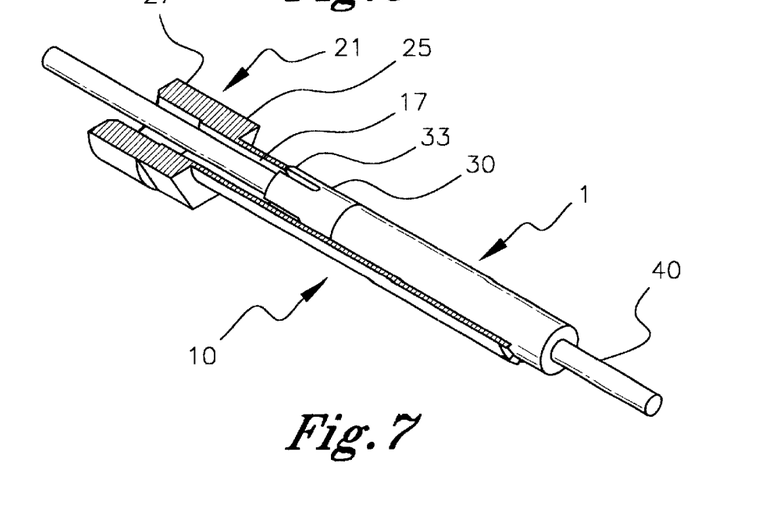
FIG. 7 shows a view similar to that of FIG. 6 but depicting a longitudinal cross-section through the coring reamer so that one may view a bone core within the coring reamer that has pushed the flared bushing in the proximal direction.

With particular reference to FIGS. 6 and 7, as understood by those skilled in the art, the guide pin 40 is driven into a bone surface at the surgical site where the surgeon desires to create a bone tunnel. The bushing 30 is slidably received over the guide pin 40 and the reamer 10 is advanced over the guide pin 40 until the bushing 30 is inserted just within the distal end thereof as seen in FIG. 6. In this configuration, the reamer 10 is advanced in the distal direction of the guide pin 40 until the teeth 15 of the reamer 10 engage the surface of the bone where the tunnel is to be created. In the preferred embodiment, the bushing is pre-assembled with the reamer and is shipped to the user in this configuration.

The handpiece (not shown) is then activated and the surgeon advances the reamer 10 in the distal direction to cause a bone tunnel to be created in the bone (not shown). As this process is taking place, the reamer 10 advances in the distal direction relative to the bushing 30 as seen in FIG. 7. The bone core 1 created through action of the reamer 10 advancing in the distal direction occupies the passageway 17 of the reamer 10, the bone core thereby pushing the bushing 30 in the proximal direction as shown in FIG. 7. The line contact between the proximal end 33 of the bushing 30 and the walls of the passageway 17 create a minimal amount of frictional interaction therebetween, thereby requiring the surgeon to use a minimal amount of force necessary to advance the reamer 10 within the bone tissue to cut the tunnel therewithin.

Once the tunnel has been created through the bone, the pin 40 is removed from the bone with the coring reamer 10 attached thereto. Thereafter, the pin 40 is pulled out from the reamer 10 leaving the reamer 10 with the bone core 1 and the bushing 30 captured therewithin. At this point, the package described hereinabove is employed. (As will be understood below, the package is used in the preferred embodiment to ship the reamer/bushing assembly and attach it to the handpiece.)

With reference, now, to FIGS. 8–14, the package for the coring reamer is generally designated by the reference numeral 50 and is seen to include a transparent tube 51 having a closed distal end 53 and an open proximal end 55 closable by a cap 57 having a distal cylindrical portion 59 receivable within the open end 55, and a proximal gripping portion 61 having an enlarged periphery with a plurality of concavities 63 in the preferred embodiment for best facilitating gripping of the gripping portion by the fingers of the user for a purpose to be described in greater detail hereinafter.

Figure 8:
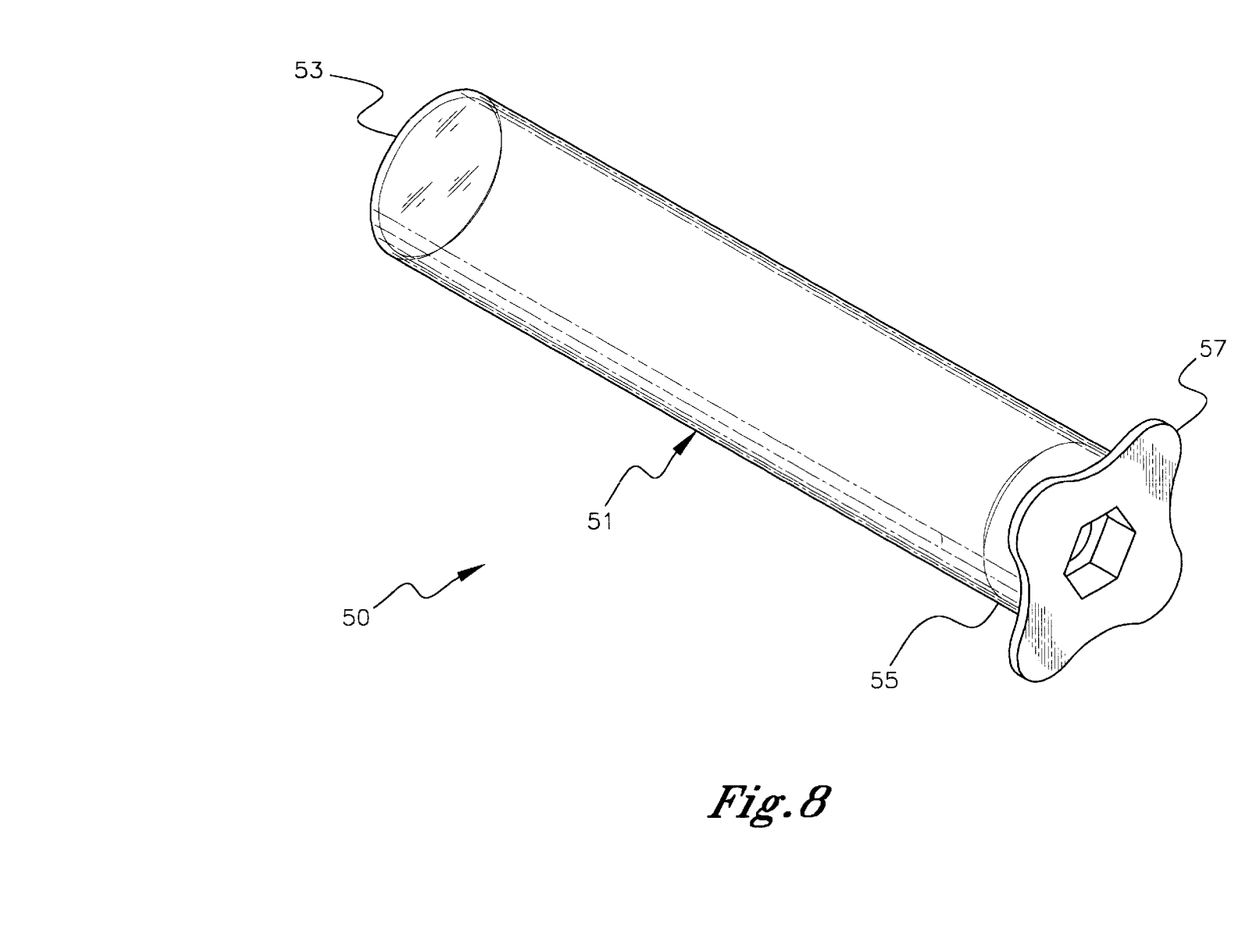
FIG. 8 shows a side perspective view of a package used to store the reamer assembly and facilitate removal of the bone core therefrom.
Figure 9:
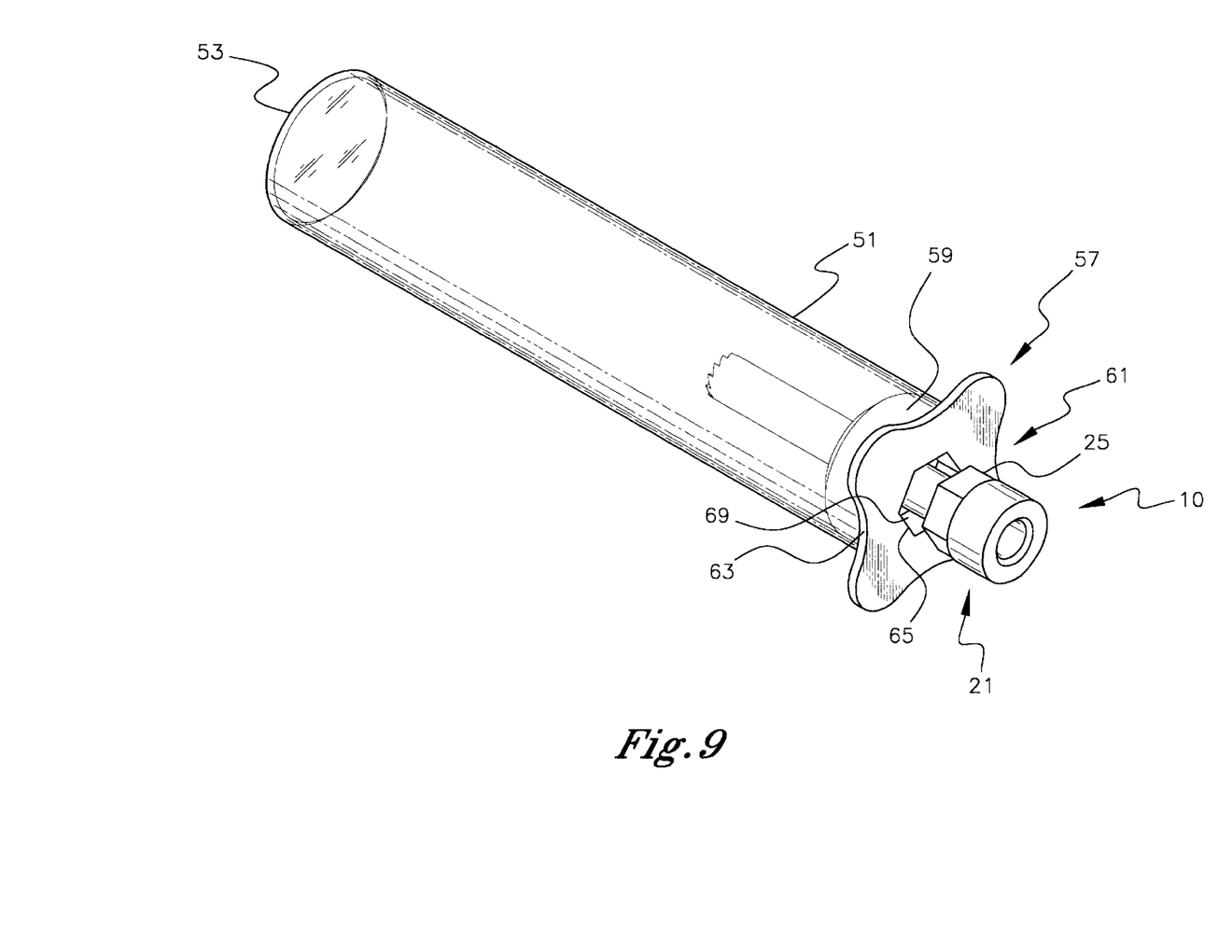
FIG. 9 shows a further perspective view with the coring reamer being placed within the package.

With reference to FIGS. 8 and 9, in particular, the cap 57 has an opening 69 therethrough which, at least at the proximal end thereof, has a hexagonal configuration 65 sized and configured to receive the distal hexagonal portion 25 of the proximal coupling 21 of the coring reamer 10 for a purpose to be described in greater detail hereinafter. Opening 69 is tapered distally to provide a friction fit to hold the reamer 10 during shipment.

Figure 10:
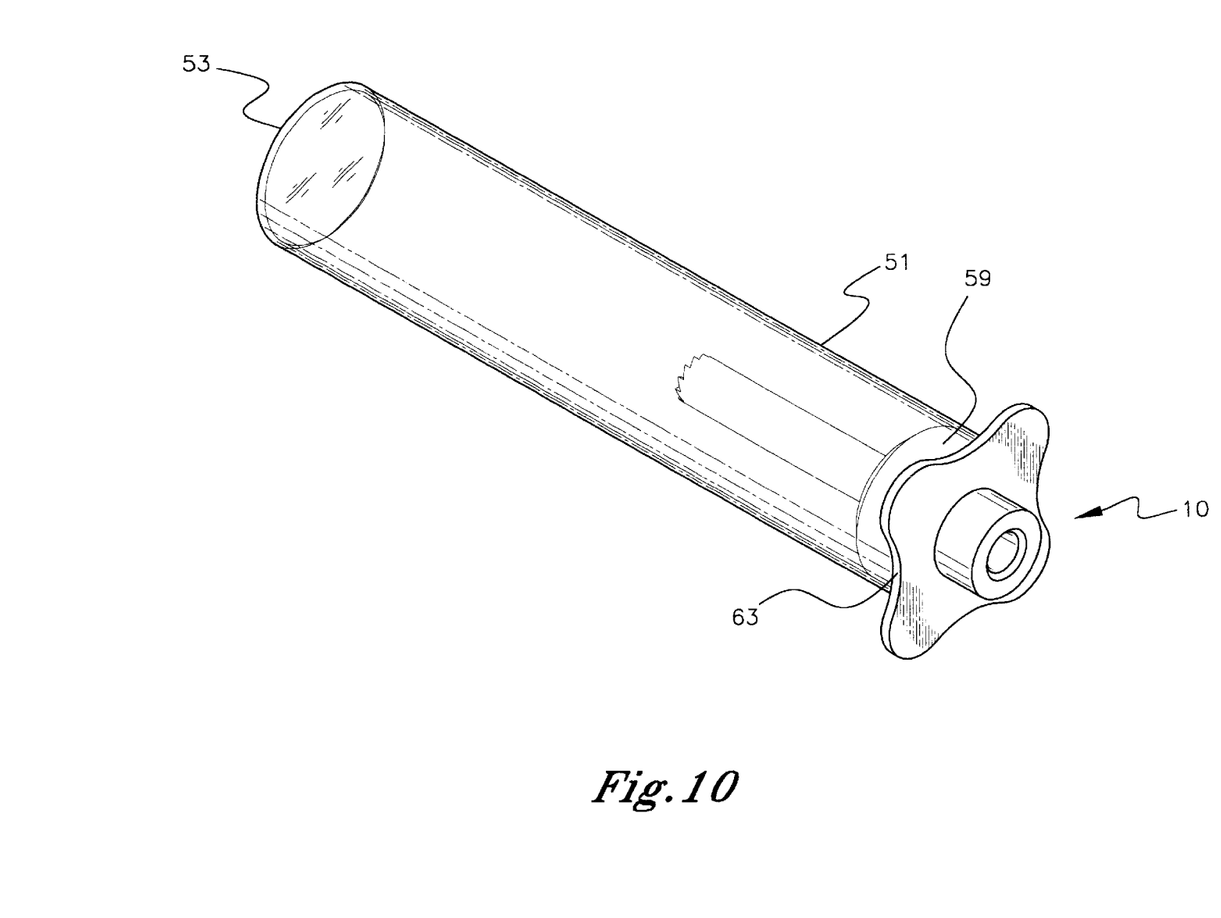
FIG. 10 shows a further view with the coring reamer placed within the package.

As seen in FIGS. 9 and 10, when viewed together, the coring reamer 10 is received within the opening 69 of the cap 57 but with the distal hexagonal portion 25 of the proximal coupling 21 thereof received within the hexagonal configuration 65 in the cap 57. In this way, the coring reamer 10 containing bushing 30, is non-rotatably received within the opening 69 of the cap 57 and suspended in tube 51 in a cantilevered manner.

Figure 11:
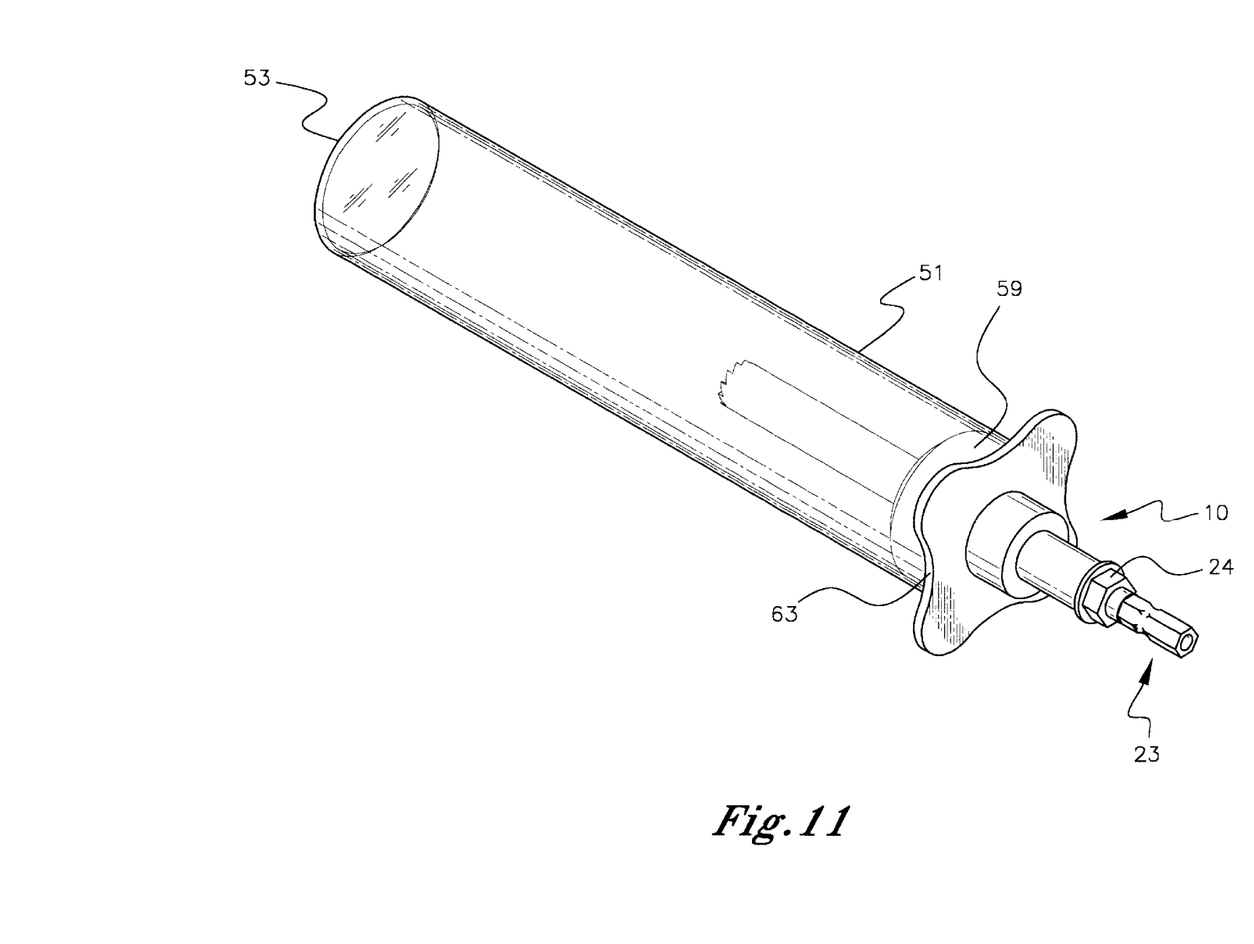
FIG. 11 shows a view similar to that of FIG. 10 but with the adapter assembly used to couple the coring reamer to a handpiece shown in its installed position.
Figure 12:
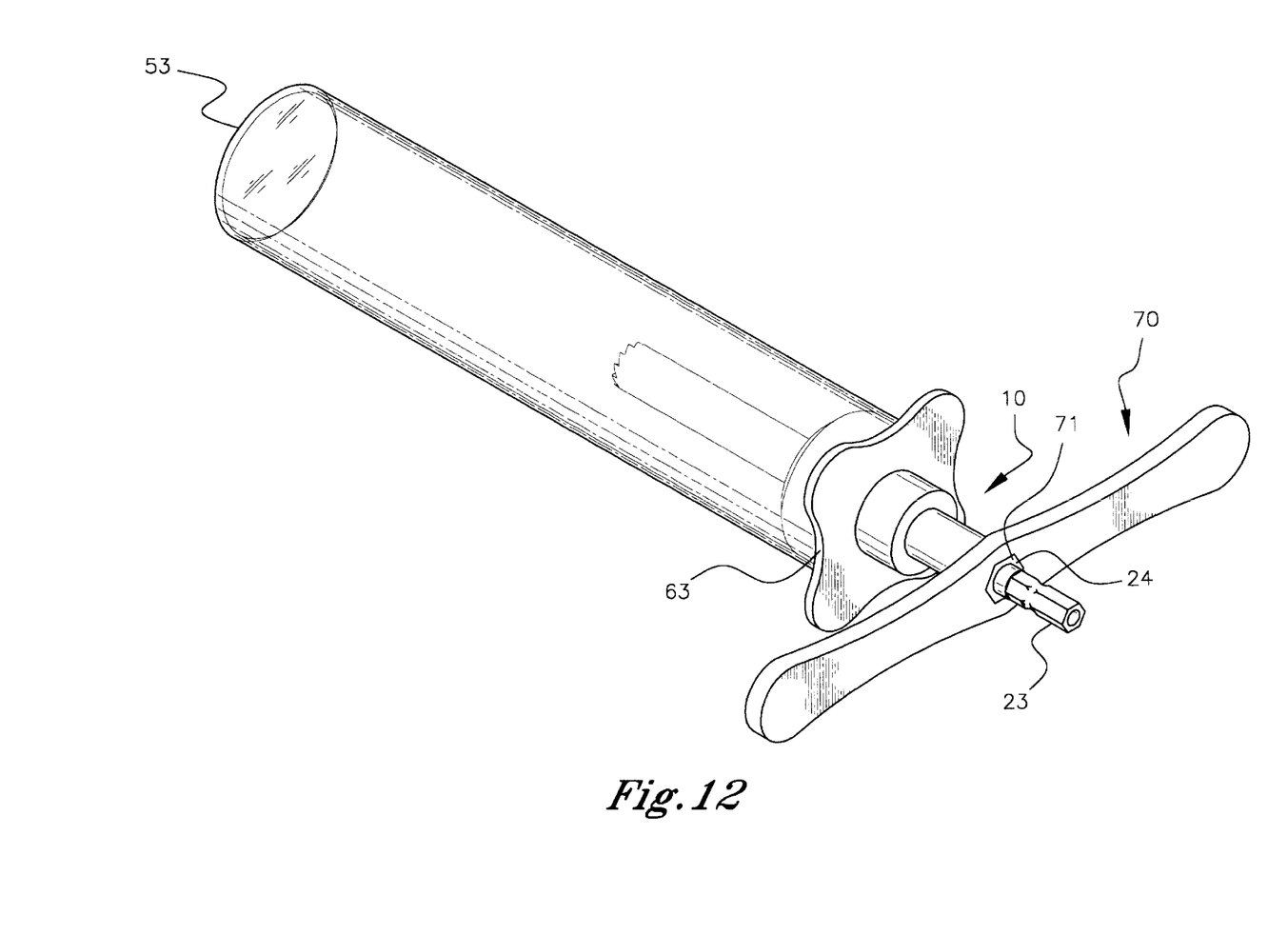
FIG. 12 shows a wrench employed to attach and remove the adapter from the coring reamer.

With reference to FIG. 11, the coring reamer 10 is seen with the adapter 23 threadably coupled thereto, which adapter 23 is adapted to couple the coring reamer 10 to a handpiece (not shown) in a manner well known to those skilled in the art. The configuration of FIG. 11 represents two situations: (1) the initial joining of the adapter to the reamer/bushing/package assembly prior to attachment of the adapter to a handpiece, and (2) the post-tunnel-formation configuration in which the reamer/bushing/bone/adapter assembly (after disconnection from the handpiece)is placed in the package for further disassembly. In the former situation, when the adapter 23 and reamer 10 are coupled to the handpiece, the package 50 is removed. With reference to FIG. 12, a wrench 70 has an elongated shape with a central hexagonal opening 71 sized to couple to a hexagonal portion 24 of the adapter 23. Thus, it should be understood that with the coring reamer 10 non-rotatably received within the cap 57, the user may grip the concave portions 63 of the cap 57 to thereby fix the rotative position of the coring reamer 10, whereupon the wrench 70 may be rotated to attach or remove the adapter 23 from the coring reamer 10, as needed.

Figure 13:
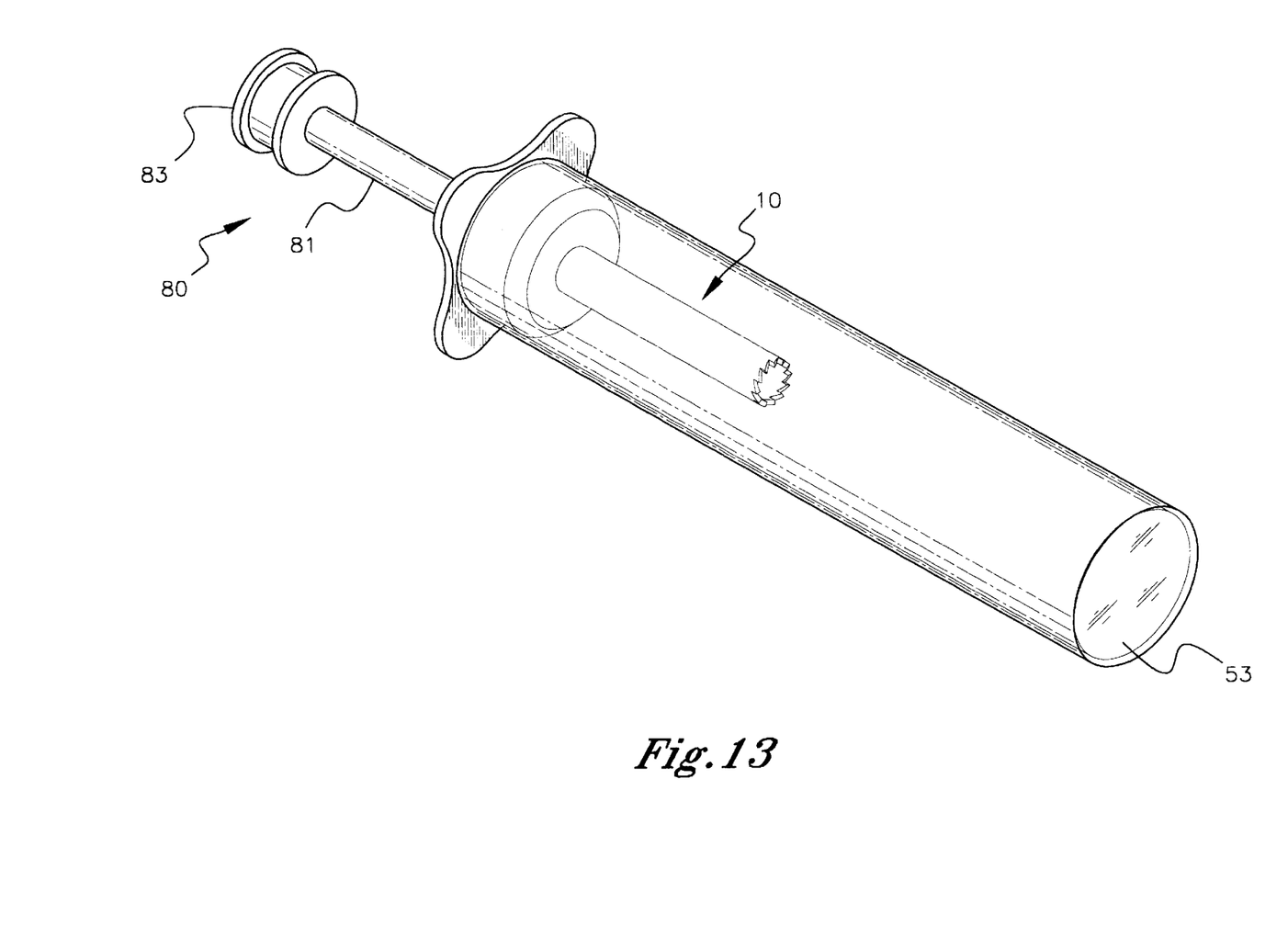
FIG. 13 shows a perspective view depicting the use of a plunger to push a bone core and the flared bushing from within the coring reamer.
Figure 14:
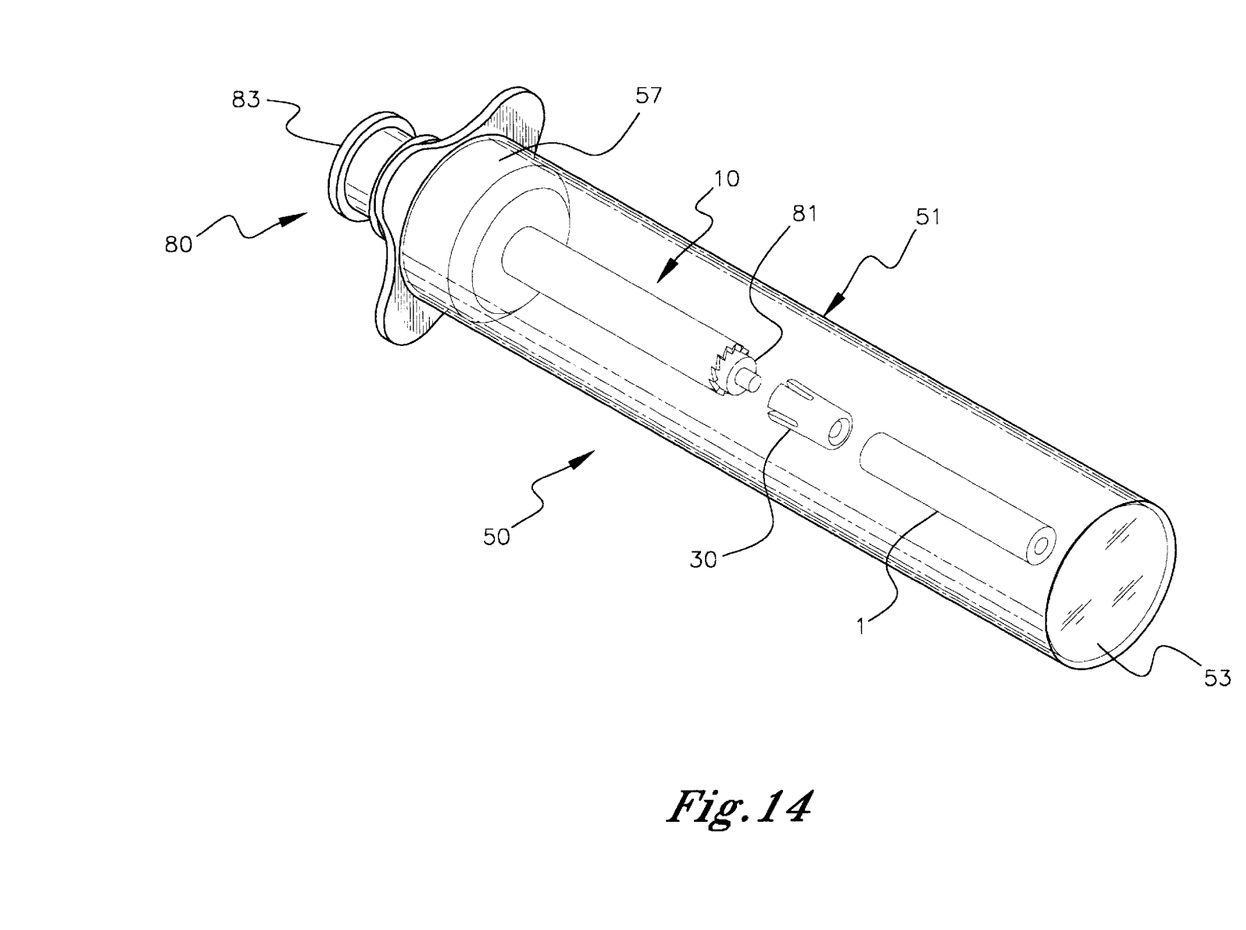
FIG. 14 shows a perspective view similar to that of FIG. 13 but with the plunger fully inserted within the coring reamer and the bone core and flared bushing removed therefrom.

With the coring reamer 10 freed of the adapter 23, as depicted in FIGS. 9, 10, 13 and 14, a plunger 80 may be used to remove the bone core 1 and the bushing 30 from within the reamer 10. The plunger 80 includes an elongated stem 81 and a proximal gripping portion 83 (FIGS. 13 and 14). The plunger 80 is inserted through the proximal end of the reamer assembly as shown in FIG. 13 and is advanced in the distal direction through the passageway 17 of the coring reamer 10 to engage bushing 30 (as facilitated by "lead-in" 39) to push the bone core 1 and the flared bushing 30 from the distal end of the reamer 10. The "lead-in" surface 39 centers the pushing force relative to the bone core. This is depicted in FIG. 14 which shows the bone core 1 and the bushing 30 captured within the tube 51. The plunger 80 may then be pulled proximally from the coring reamer 10 and the coring reamer 10, bushing 30 and bone core 1 all remain stored within the tube 51 until the core is ready for use.

With the above description of the coring reamer 10 and the package 50 having been described in detail, the method of practicing the present invention should be self-evident.

In summary, the following steps are employed:

(1) The pin 40 is driven into a bone tissue (not shown).

Figure 5:
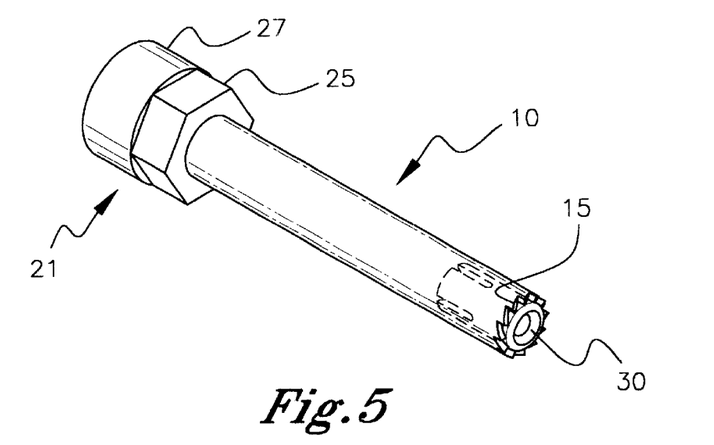
FIG. 5 shows a perspective view of the coring reamer with the flared bushing in phantom within the distal end thereof.

(2) Thereafter, the reamer/bushing assembly is advanced over the guide pin, or alternatively, the bushing 30 is advanced over the pin 40 and the coring reamer 10 is advanced over the pin until the bushing 30 is received within the distal end of the reamer 10 (FIGS. 5 and 6).

(3) Thereafter, the coring reamer 10 is coupled to a handpiece via an adapter 23 (FIG. 11) and the handpiece is activated rotating the reamer so that, while guided by the guide pin 40 and the bushing 30, a tunnel is created within the bone tissue with a bone core being generated and received within the passageway 17 through the coring reamer 10 as the reamer 10 advances into the bone tissue (FIG. 7).

(4) Once the bone tunnel has been created, the pin 40 and the reamer 10 including the bone core 1 and the flared bushing 30 are removed from the bone tissue. The pin 40 is removed from the reamer 10 and the reamer 10 is installed in the package through the opening 69 within the cap 57 of the package assembly 50.

(5) The wrench 70 is used to remove the adapter 23 from the coring reamer 10 while the user grips the surfaces 63 of the cap 57 of the package assembly 50.

(6) Thereafter, the plunger 80 is inserted through the proximal end of the coring reamer 10 and is advanced through the passageway 17 removing the bone core 1 and the bushing 30 from the distal end thereof.

(7) Thereafter, the coring reamer 10, the bushing 30 and package 50 may be disposed of properly while bone core may be used as desired.

As mentioned above, package assembly 50 also can be used to ship and store the coring reamer and bushing prior to use. If so, adapter 23 is applied to the coring reamer 10 by wrench 70 as shown in FIGS. 11 and 12. After use, the coring reamer, bushing and bone core are returned to the same package for disassembly.

The reamer, bushing and package are intended to be disposable. The reamer and bushing are preassembled and shipped within the package. Therefore, the user simply needs to attach the adapter to the proximal end of the reamer and attach the entire assembly (adapter, reamer, bushing and package) onto the handpiece, and then the package may be removed. This prevents anyone from having to touch the reamer and also prevents the reamer from being accidentally dropped or nicked or otherwise detrimentally affected. Pre-packaging of the bushing within the reamer is done with a fixture (not shown) which squeezes the proximal end 33 of the bushing. This prevents the reamer from scraping the surface of the bushing which might create particulate matter. Shipping the bushing within the reamer prevents the user from ever having to assemble these pieces.

An invention has been disclosed in terms of apparatuses and process for their practice which fulfill each and every one of the objects of the invention as set forth hereinabove, and provide a new and useful guide bushing for coring reamer, storage package for reamer assembly, and method of using, of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

What is claimed is:

1. In a coring reamer including a cylindrical body with a cylindrical passageway extending therethrough, the improvement comprising a guide bushing having a passage extending longitudinally therethrough, said passage being sized to slidably receive a guide pin therethrough, said guide bushing having an external surface tapered from a larger diameter at one end thereof to a smaller diameter at another end thereof, said larger diameter being equal to or less than a diameter of said passageway, whereby said one end of said bushing engages an inner wall of said passageway with a line contact.

2. The reamer of claim 1, wherein said one end of said bushing comprises a distal end thereof.

3. The reamer of claim 1, wherein said passage includes a distal termination comprising a frusto-conical surface diverging in a distal direction thereof.

4. The reamer of claim 1, wherein said external surface of said bushing is at least partially frusto-conical.

5. The reamer of claim 4, wherein said external surface tapers outwardly in a proximal to distal direction.

6. The reamer of claim 2, wherein said another end of said bushing comprises a proximal end thereof.

7. A method of performing surgery including the steps of:
   a) driving a guide pin into bone tissue;
   b) sliding a bushing over said guide pin, said bushing having a passage extending therethrough and an external surface tapered from a smaller diameter at a first end thereof to a larger diameter at a second end thereof;
   c) sliding a coring reamer over said bushing, said coring reamer having a cylindrical body with a cylindrical passageway extending therethrough and adapted to engage said second end of said bushing;
   d) rotating and advancing said coring reamer to cut a bone tunnel while said coring reamer is guided on said guide pin by said bushing.

8. The method of claim 7, after said rotating and advancing step, including the step of removing said guide pin and coring reamer from said bone tissue.

9. The method of claim 8, after said removing step, including the step of inserting a distal end of said coring reamer through an opening of a cap of a tube receiving said coring reamer.

10. The method of claim 9, after said inserting step, including the step of removing an adapter from a proximal end of said coring reamer.

11. The method of claim 10, after said removing step, including the step of inserting a plunger through said cylindrical passageway in said coring reamer to remove said bushing and a bone core therefrom, said bushing and bone core falling into said tube.

12. The method of claim 10, wherein said removing step includes the steps of providing said cap with an enlarged periphery and gripping surfaces and gripping said gripping surfaces while removing said adapter.

13. The method of claim 12, wherein said removing step further includes the steps of providing said opening with a non-circular portion configured to non-rotatably receive a non-circular proximal end of said coring reamer.

* * * * *